United States Patent [19]

Liao

[11] Patent Number: 4,463,752

[45] Date of Patent: Aug. 7, 1984

[54] LIMB-SUPPORTING FRAME WHICH IS MOVABLE AND EASY TO BE DISMANTLED

[76] Inventor: Kuo M. Liao, 4th Fl., 7, Lane 85, Kuang Fu North Rd., Taipei, Taiwan

[21] Appl. No.: 437,626

[22] Filed: Oct. 29, 1982

[51] Int. Cl.³ .............................................. A61F 5/04
[52] U.S. Cl. ................................................ 128/87 R
[58] Field of Search ...................... 128/87 R, 80 R, 83, 128/84 R, 85

[56] References Cited

U.S. PATENT DOCUMENTS

| | | | |
|---|---|---|---|
| 76,382 | 4/1868 | Barnes | 128/85 |
| 590,625 | 9/1897 | Paquette | 128/85 |
| 650,774 | 5/1900 | Barton | 128/85 |
| 4,174,709 | 11/1979 | Maddux | 128/87 R |

Primary Examiner—John D. Yasko
Attorney, Agent, or Firm—Tak K. Sung

[57] ABSTRACT

The present invention relates to a novel limb-supporting frame which is movable and easy to be dismantled. Especially to a combination of a shank-supporting frame, an ankle-supporting frame, and a leg-supporting frame. The said frames are fixed by means of the threads of the frames, collars, and packing pieces; thus, the ankle-supporting frame and the shoe attached to the ankle-supporting frame can be taken off, and the limb-supporting frame is easy to be dismantled and combined. There is a joint between the shank-supporting frame and the leg-supporting frame, so that the shank-supporting frame can be swung backward. Moreover, the length of the limb-supporting frame according to the present invention can be adjusted in accordance with the growth of the skeleton.

1 Claim, 3 Drawing Figures

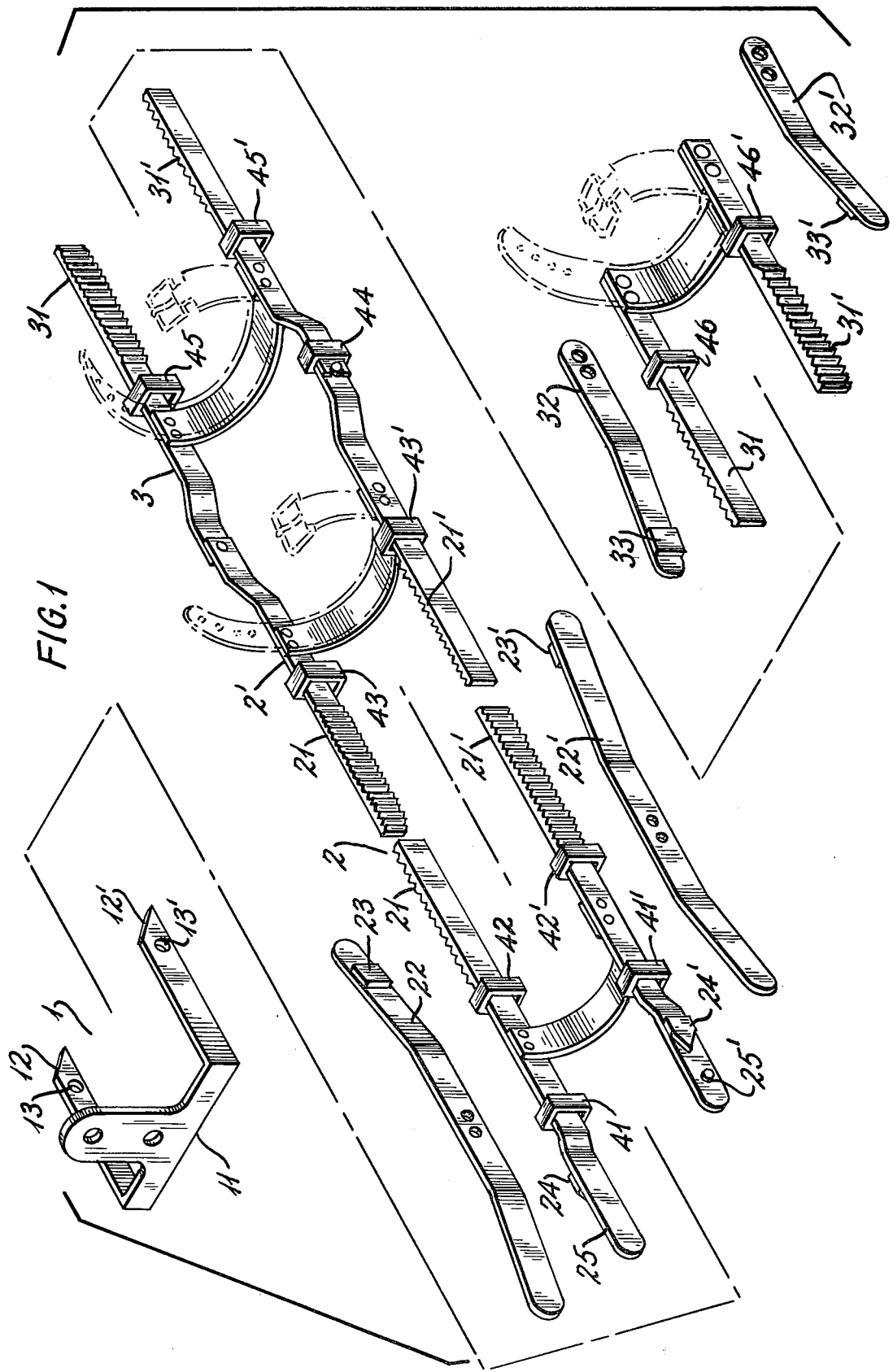

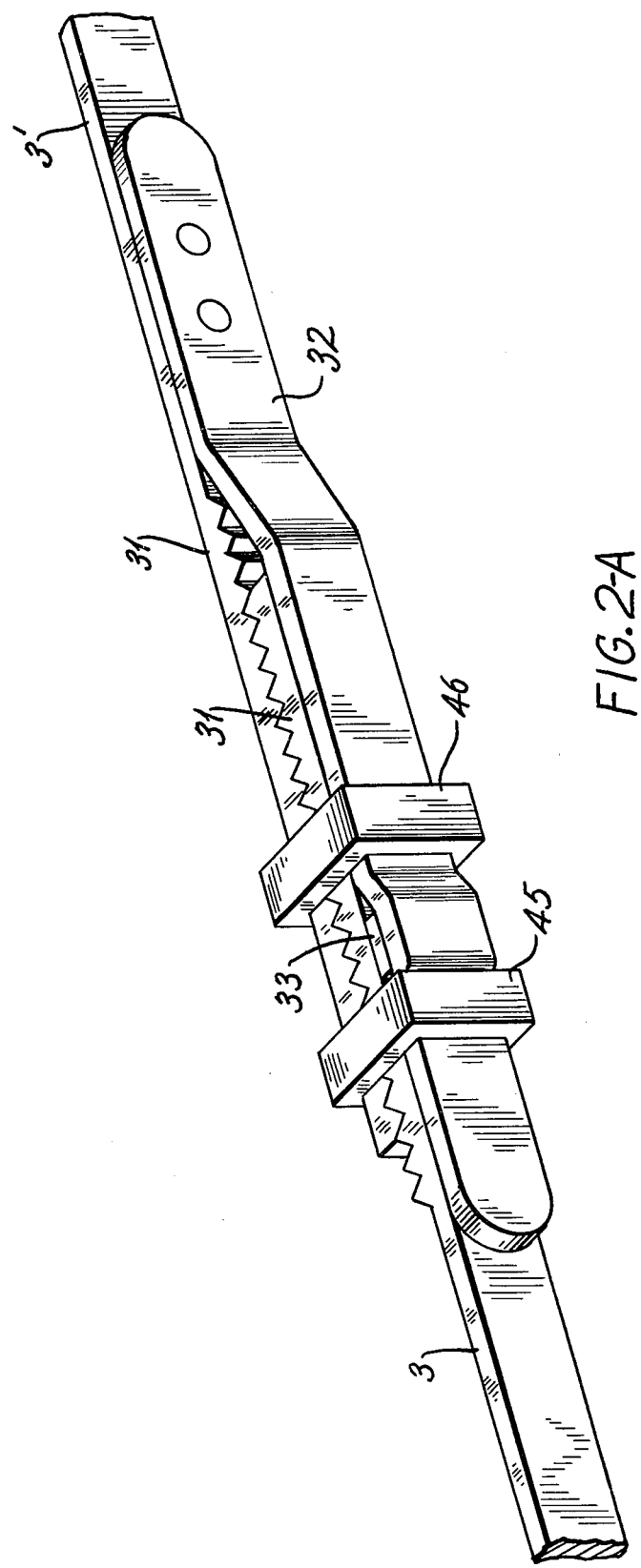

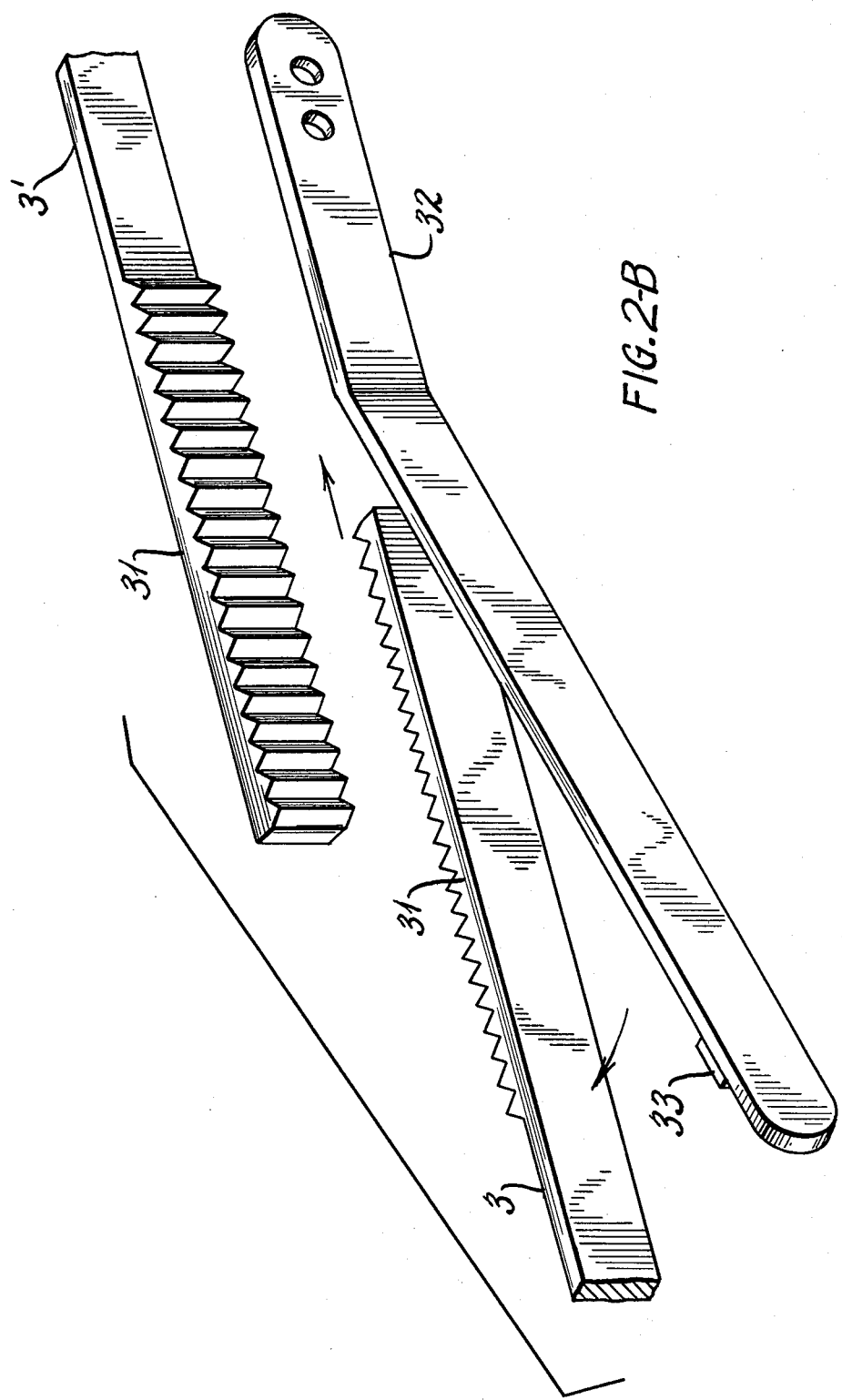
FIG. 2-B

LIMB-SUPPORTING FRAME WHICH IS MOVABLE AND EASY TO BE DISMANTLED

BACKGROUND OF THE INVENTION

The drawbacks of the conventional limb-supporting frames are as follows:

(1) The limb-supporting frame and the shoe are formed as a whole body, so that it is very inconvenient to wear or take off the shoe.

(2) By reason that the limb-supporting frame being fixed to the shoe, it is inconvenient to take off the shoe in the occasion that it is necessary to take off the shoe temporarily.

(3) Since the limb-supporting frame and the shoe are formed as a whole body, the shoe cannot be changed.

(4) Since there are only a collar mounted to the front of the limb and a transverse supporting plate mounted to the rear of the limb, the limb-supporting frame cannot be fixed steadily, so that the limb-supporting frame is easy to be loosened and chafes the limb.

The skeletons of most patients of poliomyelities still continue to grow, so that the limb-supporting frame must be changed in order to adapt to the limb; thus, the economic burden of the user is much increased.

For the reasons stated above, the inventor of this invention through many experiments invents a novel limb-supporting frame which is moveable and easy to be dismantled.

SUMMARY

The main object of the present invention is to provide a novel limb-supporting frame which is movable and easy to be dismantled; by means of collars, packing pieces, and the threads of the shank-supporting frame and the leg-supporting frame, the frames are tightly fixed and can be adjusted.

The advantages of the limb-supporting frame according to the present invention are as follows:

(1) It is convenient to wear or to take off the limb-supporting frame according to the present invention.

(2) The limb-supporting frame according to the present invention is easy to be dismantled.

(3) The shoe attached to the limb-supporting frame according to the present invention can be changed.

(4) The limb-supporting frame according to the present invention can be made of F.R.P. and is protected by the belts so as to prevent looseness and friction with the leg.

(5) The length of the limb-supporting frame according to the present invention can be adjusted, so that it can be adapted to the growth of the skeleton.

(6) Since the ankle-supporting frame, the shank-supporting frame, and the leg-supporting frame of the limb-supporting frame according to the present invention are movable, the component parts of the present invention can be changed in case they are broken.

(7) The limb-supporting frame is easy to be operated, so that the user can save much time and much strength. As the description stated above, the limb-supporting frame really aims at the drawbacks of conventional limb-supporting frame and improves the efficiency. Since the structure of the present invention is simple, the manufacturing cost can be decreased and the life can be prolonged. Thus, the prevent invention really has the properties of practicality and novelty.

BRIEF DESCRIPTION OF THE DRAWING

FIG. 1 is a fragmentary perspective view of the present invention;

FIG. 2A shows the combination of the upper leg-supporting frame and the lower leg-supporting frame;

FIG. 2B shows how to combine the upper leg-supporting frame and the lower leg-supporting frame.

DETAILED DESCRIPTION OF THE PREFERRED EMBODIMENT

With reference to FIG. 1, there is shown a fragmentary perspective view of the present invention. On shank-supporting frame is mounted movable and detachable shoe frame (1) which can be used for changing shoe. Anke-supporting frame (1) is connected to block (24) by means of arm (12). Protuberance (25) is joined to hole (13) in the manner that protuberance (25) can be moved with respect to hole (13), so that the shoe attached to ankle-supporting frame (1) can be taken off when ankle-supporting frame (1) is swung backward. Belt (5) is used for fastening the limb-supporting frame on the leg. Shank-supporting frame (2), and leg-supporting frame are provided with threads (21, 21', 31, 31') respectively. There are four elastic packing pieces (22, 22', 32, 32') and eleven collars (41, 41', 42, 42', 43, 43', 44, 45, 45', 46, 46'). Arms (12, 12') of ankle-supporting frame (1) are connected with blocks (24, 24'), protuberances (25, 25'), and packing pieces (22, 22'). Packing pieces (22, 22') are pressed on lower shank-supporting frame (2), and collars (42, 42', 41, 41') are encased into packing pieces (22, 22') and lower shank-supporting frame (21), so that the effect of clamping is obtained. Shank-supporting frame is divided into lower shank-supporting frame (2) and upper shank-supporting frame (2'). Threads (21, 21') of lower shank-supporting frame are engaged with threads (21, 21') of upper shank-supporting frame (2'). By means of collars (43, 43') and packing pieces (22, 22') of which the two ends are bent outward, lower shank-supporting frame (2) is fixed to upper shank-supporting frame (2'); and by means of rubber protuberances (23, 23', 33, 33'), slippage between the two frames (2, 2') is impossible to happen. Collars (41, 41' 44) are not used for clamping the threads. Collars (41, 41') are used for vertically fixing ankle-supporting frame (1) which can be swung backward. A joint is formed between upper shank-supporting frame (2') and lower leg-supporting frame (3), so that the shank-supporting frame can be swung backward. Collar (44) is used for fixing upper shank-supporting frame (2') to lower leg-supporting frame so as to be able to stand up vertically. By means of the engagement of threads (31, 31') of upper leg-supporting frame (3') and threads (31, 31') of lower leg-supporting frame (3), and the fixation of packing pieces (32, 32'), leg-supporting frames (3, 3') can be adjusted and fixed.

Please refer to FIG. 2A and FIG. 2B. Since complicated component parts are replaced by elastic packing piece (22) (by way of example only) in the clamping of the present invention. The cost can be much decreased. First, collar (43) is used for pressing elastic packing piece (32) to the back of threads (31'); collar (42) is used for fixing threads (31, 31') and packing piece (32); and then collars (45, 46) are moved to the appropriate positions; leg-supporting frame (3, 3') is fixed. The reason why leg-supporting frame can be fixed is that the expanding force of elastic packing piece (32) causes collar (45) to clamp threads (31, 31') tightly. Thus leg-supporting frame (3, 3') will not slip in vertical direction when the lengths of the leg-supporting frame (3, 3') are adjusted. Since threads (31, 31') are fixed by collar (45). It is impossible for leg-supporting frames (3, 3') to move. Upper leg-supporting frame (3') can be dismantled by taking off collar (45). Thus the movements of ankle-supporting frame (1), and shank-supporting frames (3, 3') are controlled by the collars. By means of packing pieces (22, 22') and collars (41, 41'). Ankle-supporting frame (1) can be fixed or loosened, so that ankle-supporting frame (1) can be swung backward. By means of the combination of packing pieces (22, 22') and threads (21, 21'). The length of shank-supporting frame (2, 2') can be adjusted. Also, by means of the combination of packing pieces (32, 32') and threads (21, 21'). The length of leg-supporting frame (3, 3') can be adjusted. There is a movable joint between upper shank-supporting frame (2') and lower leg-supporting frame (3), so that the shank-supporting frame can be swung backward.

I claim:

1. A limb-supporting frame which is movable and easy to be dismantled, mainly comprising an ankle-supporting frame, a shank-supporting frame, a leg-supporting frame, and eleven collars, charaterized by the two ends of said ankle-supporting frame being provided with two arms on which there are two holes used for coupling with the blocks and the protuberances of the said shank-supporting frame, said arms being fixed to the collars, said ankle-supporting frame being able to be swung backward when the collars are loosened; said shank-supporting frame being divided into a lower shank-supporting frame and an upper shank-supporting frame, the lower part of said upper shank-supporting frame being provided with threads which are especially used for engaging with the threads provided on the lower parts of said lower shank-supporting frame in order that the shank-supporting frame can be extended or contracted, a joint being formed between the upper shank-supporting frame and the lower leg-supporting frame by means of the collar of the lower leg-supporting frame being adapted to the other arm of the upper shank-supporting frame, the threads provided on the upper part of said lower shank-supporting frame being engaged with the threads provided on the lower part of said upper shank-supporting frame, the lower part of said lower shank-supporting frame being joined to said ankle-supporting frame, a set of elastic packing pieces is mounted to the sides opposite to the threads of the lower shank-supporting frame and the threads of the upper shank-supporting frame, two ends of said elastic packing piece being bent outward and one ends of said elastic packing piece being provided with a rubber protuberance; said leg-supporting frame being provided with an upper leg-supporting frame and a lower leg-supporting frame, the lower part of said upper leg-supporting frame and the upper part of said lower leg-supporting frame being provided with threads, the threads of said upper leg-supporting frame being especially designed for engaging with the threads of said lower leg-supporting frame, said upper leg-supporting frame and said lower leg-supporting frame being fixed together by the collars, a joint being formed between said lower leg-supporting frame and said upper shank-supporting frame, and at the side opposite to the threads of said lower leg-supporting frame being mounted a packing piece which is bent at one end and has a rubber protuberance at one end; said collars being divided into two groups, one group of the collars being especially used for loosening said ankle-supporting frame so as to enable the joint of said ankle-supporting frame and said shank-supporting frame to swing backward or used for fixing said ankle-supporting frame and said shank-supporting frame vertically, the second group of the collars of which four collars are used for pressing the packing pieces to the side opposite to the threads of said lower leg-supporting frame and of which the other four collars are used for fixing the threads of said lower leg-supporting frame and the threads of said upper leg-supporting frame and said packing pieces together.

* * * * *